United States Patent [19]

Chandler

[11] Patent Number: 4,665,034

[45] Date of Patent: May 12, 1987

[54] DEVICE FOR PERFORMING QUALITATIVE ENZYME IMMUNOASSAYS

[75] Inventor: Howard M. Chandler, Mississauga, Canada

[73] Assignee: Allelix Inc., Mississauga, Canada

[21] Appl. No.: 551,906

[22] Filed: Nov. 15, 1983

[51] Int. Cl.⁴ .................. C12M 1/00; C12M 1/24; G01N 33/544; G01N 1/48

[52] U.S. Cl. .................. 435/287; 435/296; 435/810; 436/535; 436/808; 436/818; 422/57; 422/58; 422/61; 422/68; 422/99

[58] Field of Search .............. 436/535, 808, 818; 435/296, 806, 7, 810, 287; 422/57, 58, 61, 68, 69, 71, 100

[56] References Cited

U.S. PATENT DOCUMENTS

| Re. 31,006 | 8/1982 | Schuurs et al. | 435/7 |
|---|---|---|---|
| 4,276,048 | 6/1981 | Leaback | 435/296 X |
| 4,585,623 | 4/1986 | Chandler | 435/296 X |

FOREIGN PATENT DOCUMENTS

WO82/02211  7/1982  PCT Int'l Appl. .
WO83/01119  3/1983  PCT Int'l Appl. .

OTHER PUBLICATIONS

UCG-Beta Stat—1980 Horner.

Primary Examiner—Sam Rosen
Assistant Examiner—Shawn P. Foley
Attorney, Agent, or Firm—Ridout & Maybee

[57] ABSTRACT

The invention relates to a device and method for performing qualitative enzyme immunoassays. The device comprises at least one tube having antibody, antigen or hapten attached to an internal surface thereof. A first syringe is connectable to a first end of the tube or tubes and supplies a flow of test liquid therethrough. A second syringe having a two piston arrangement is connected to the tube so as to allow a first wash solution followed by an enzyme conjugate solution to be flowed therethrough. Finally a third syringe, also having a two piston configuration, is connected to the tube so as to allow a second wash solution followed by an enzyme substrate and metabolite indicator solution to be flowed therethrough.

13 Claims, 3 Drawing Figures

DEVICE FOR PERFORMING QUALITATIVE ENZYME IMMUNOASSAYS

The present invention relates to a device and method for performing qualitative enzyme immunoassays. The invention provides a portable compact device which may be used by an untrained person or which is suitable for use by professional personnel in the field or elsewhere when a quick determination is required for diagnostic purposes. The device has broad applicability for enzyme immunoassays, particularly qualitative assays where a simple diagnosis is requested. For example, in human or veterinary medicine, it may be used for recognition of diseases by detection of antigens or specific antibody in body fluids or tissue extracts. In agriculture, the device can, for example, be used for the detection of pesticide residues in soil extracts or pathogenic organisms in plant tissues.

In its preferred form, the invention may be used to detect the presence of an antigen or hapten in urine or blood. This assay is accomplished by the known method of contacting the sample with an antibody specific to the antigen or hapten being assayed for, which antibody is attached to a solid support such as the wall of a tube. Antigen which is captured by the fixed antibody is then detected by contacting the solid phase with an antibody/enzyme conjugate followed by treatment with an enzyme substrate and suitable indicator.

The present device is capable of detecting the substance being assayed for in lower concentration and with much greater speed than has heretofore been possible with prior art devices. Prior devices for the detection of an antigen or hapten employ an antibody attached to a solid support which is contacted sequentially with static volumes of test liquid, conjugate and substrate/indicator solutions. A period of incubation must be observed for each of these contacting steps as the reactions involved are diffusion controlled. That is, the reactions take place only at the surface of the solid support and sufficient time must elapse to enable enough antigen to migrate to the reaction vessel wall to give a positive test result. Increasing the surface area to volume ratio by carrying out these reactions in a tube having a small bore reduces incubation periods to about ten minutes each.

The present device employs a method whereby a continuous flow of the various reactive solutions are passed through a tube having the antibody affixed thereto so that the principles of affinity capture and concentration are utilized. That is, the reaction at the tube wall is forced to completion quickly by continuously bathing the solid reactant with a solution having a constant concentration of the co-reactant. This also means that the sensitivity of the assay is increased since a much lower concentration of co-reactant in the test sample can be detected by this flow through method. Thus, the present invention provides significant advantages over the devices and methods previously known. In the case of a pregnancy test, discussed in detail below, the assay for the presence of human chorionic gonadotropin (HCG) in the urine may be carried out as quickly as about three minutes using the device of the invention as compared to prior art pregnancy test devices which require 20 to 120 minutes to perform the assay. Also, the present device is much simpler to use than prior devices and many fewer operations need be performed when using the device in order to carry out the assay than is required by prior devices.

It should also be clear that the present device may be used generally for all enzyme immunoassays and should not be construed as being restricted to the detection of antigens or haptens in the manner just summarized. Without limiting the possible applications of the present invention, the device may be used as suggested to detect antigen or hapten in an antibody sandwich-type assay, or a double antibody sandwich antigen assay may be used, or a competitive antigen assay can be performed.

When detection of antibody is desired, the device can be used to do a sandwich-type assay or a double antibody sandwich antibody assay. For example, in an antigen assay for $\pm$ hepatitis subunit or virus using the double antibody sandwich antigen assay, the solid phase comprises anti-hepatitis Ab type 1 (e.g. sheep), the second antibody used is anti-hepatitis Ab type 2 (e.g. rabbit), and the conjugate is anti-type 2 Ab/enzyme.

The present device is especially suitable if a large volume of test sample is available, such as urine. A particularly suitable assay using the present device is a test for the presence of HCG (human chorionic gonadotropin) in urine to determine pregnancy. Because of the aforementioned features, pregnancy can be quickly detected at an early stage by the woman herself using the present device.

Accordingly, the invention provides a device for performing an enzyme immunoassay, comprising at least one tube having an antibody, antigen or hapten attached to an internal surface thereof. A first syringe is connectable to a first end of tube or tubes for supplying a flow of test liquid therethrough, and a second syringe is connected to the first end of the tube or tubes for supplying a flow of a first wash solution followed immediately by a flow of enzyme conjugate containing solution therethrough, said second syringe having a first unattached piston and a second piston attached to a plunger, the first piston being positioned to separate the first wash solution from the conjugate solution, and said syringe also having a wall with a groove therein connecting the syringe outlet with the conjugate solution only when the first piston is fully depressed. A third syringe is connected to the first end of the tube or tubes for supplying a flow of a second wash solution followed immediately by a flow of solution containing enzyme substrate and enzyme metabolite indicator therethrough, said third syringe having a structure like that of the second syringe.

The invention also provides a method for performing an enzyme immunoassay, comprising the steps of:

attaching an antibody antigen or hapten to an internal surface of a tube;

flowing a test liquid through the tube;

flowing a first wash solution through the tube to flush out the test liquid;

flowing an enzyme conjugate solution through the tube followed by an incubation period;

flowing a second wash solution through the tube at the end of the incubation period to flush out the enzyme conjugate solution; and flowing a solution containing enzyme substrate and enzyme metabolite indicator through the tube followed by an observation period of up to about 10 minutes.

A preferred embodiment of the invention will be described with reference to the drawings in which.

Figure 1:
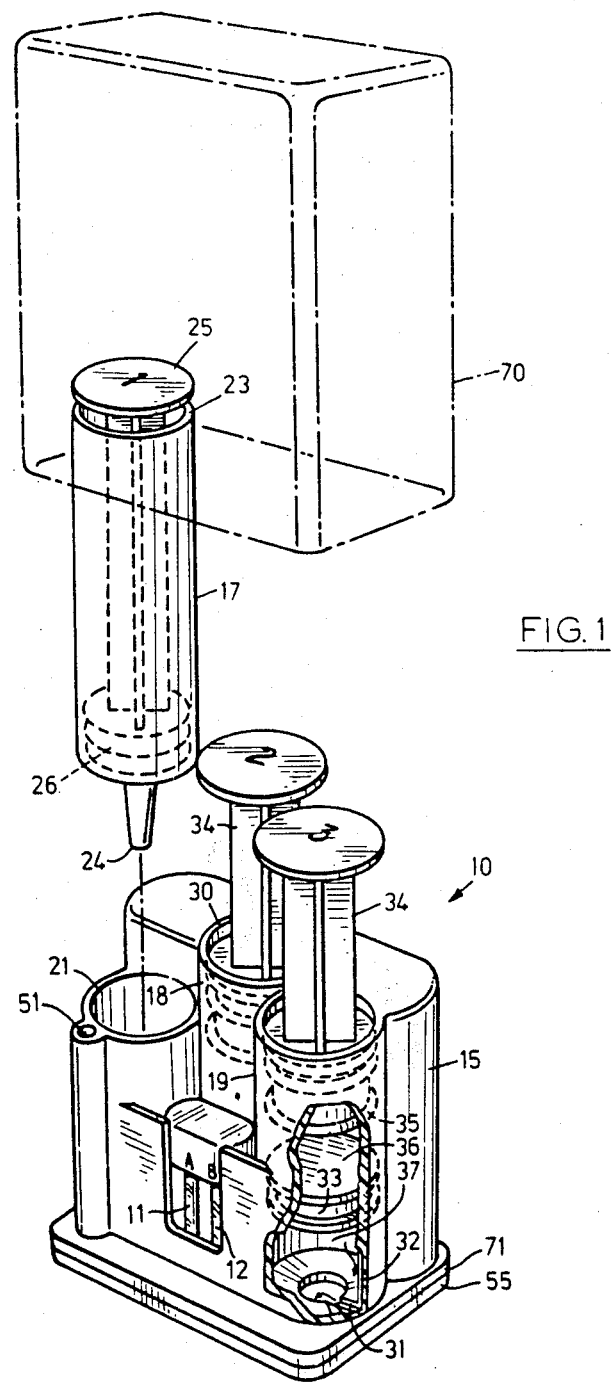
FIG. 1 is a perspective view partially cut away of the testing device.

While the present device may be used for a number of different assay applications, and indeed may be used for performing multiple assays on a single test sample, the preferred embodiment hereinafter described relates to the use of the invention for testing for pregnancy by assaying for the presence of HCG (human chorionic gonadotropin) in urine.

The preferred testing device of the invention comprises a body 10 in which is centrally disposed a tube 11 having applied to the inner wall thereof a coating of anti-HCG, i.e. HCG antibody. The anti-HCG coating is preferably covalently bonded to the tube wall, but it may be affixed by adsorption. For the purpose of providing a control, the tube 11 is connected in series to a plain uncoated tube 12. The control tube 12 is in turn connected to a waste reservoir 15 as described below. In order to make good use of the advantages of the flow through technique, it is desirable to have a surface area to volume ratio in the tube 11 as large as is practical given the various parameters surrounding the manufacture and use of the preferred device. Thus, a tube 11 on the order of about 25 mm in length having a bore of about 1 mm in diameter is quite suitable in the present context.

The various solutions required to perform the assay are passed sequentially through the tubes 11 and 12 by means of first, second and third syringes 17, 18 and 19. A test sample syringe 17 is removable from a receptacle 21 which is integral with the body 10. The test sample syringe 17 comprises a body 23 having an outlet 24 at one end and a plunger 25 having a piston 26 attached at an end thereof which may move slidably within the syringe body 23 to fill and empty the syringe 17 with a liquid test sample. A urine sample of about 5 ml is reasonable for use in the particular pregnancy test device described herein.

The body 10 preferably has two additional syringes 18 and 19 integral therewith. However, the preferred device may comprise removable syringes 18 and 19, and indeed this may be desirable in certain circumstances. The syringe 18 comprises a receptacle 30 having an outlet 31 at its lower end and a groove 32 communicating with the outlet 31 in the wall thereof. The syringe receptacle 30 is provided with an unattached piston 33 and a plunger 34 having a piston 35 attached at one end thereof. The free piston 33 is used to separate two solutions contained within the syringe receptacle 30, one solution contained in an upper portion 36 of the syringe 18 between the free piston 33 and the plunger 34, and the other solution contained in a lower portion 37 between the free piston 33 and the outlet 31. The final syringe 19 is of a structure identical to that of syringe 18.

Figure 2:
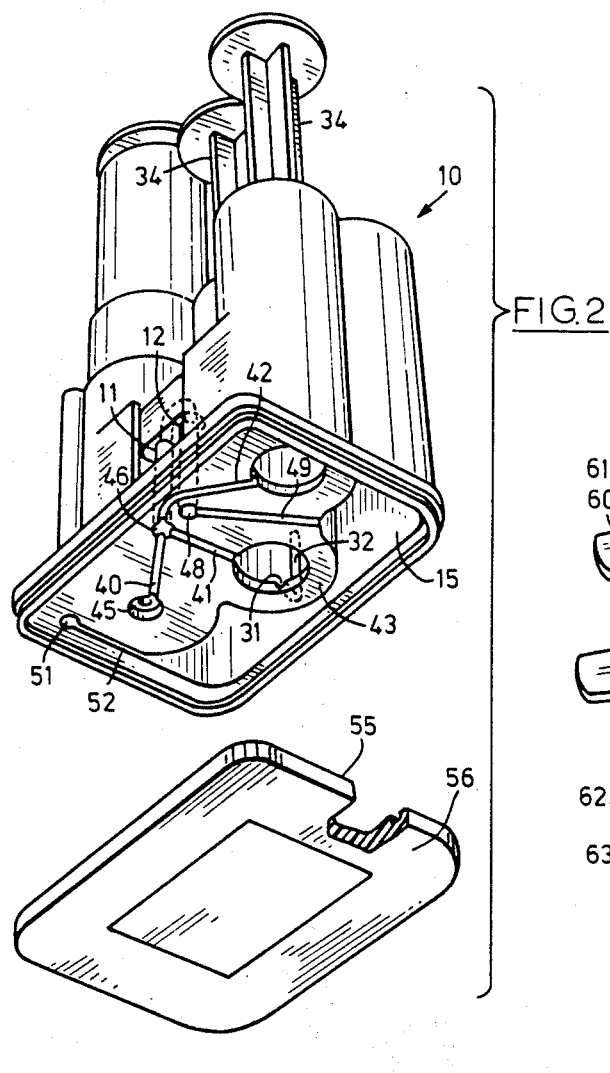
FIG. 2 is a perspective view from below the device with the bottom plate removed.

The outlets of the syringes 17, 18 and 19 are connected to the lower end of the tube 11 by means of channels 40, 41 and 42 formed in the base 43 of the body 10 (FIG. 2). The channel 40 connects an opening 45 for the outlet 24 of the sample syringe 17 to an opening 46 for the tube 11. Likewise channels 41 and 42 connect the outlets 31 of syringes 18 and 19 with the opening 46. An opening 48 is provided in the base 43 for the outlet end of the control tube 12 which is in turn connected to the waste reservoir 15 by means of a channel 49. Finally, a vent shaft 51 is provided in the body 10, the lower end of which is connected to the waste reservoir 15 by means of a slot 52 in the body 10. The base 43 comprises a flat surface which is sealed to the unbroken flat surface 55 of a bottom plate 56 for the device.

For the purpose of providing a pregnancy testing device, the syringe 18 is filled with a solution containing an enzyme/anti-HCG conjugate in the upper portion 36. A urease/anti-HCG conjugate is preferred in this regard. The lower portion 37 of the syringe 18 is filled with a wash solution compatible with the subsequently added conjugate solution.

The upper portion 36 of the syringe 19 is filled with a solution containing substrate for the enzyme of the conjugate and an indicator to detect the conversion of substrate by the enzyme in the tube 11. Preferably, the substrate is urea which is metabolized by the urease of the conjugate to give ammonia and carbon dioxide. The pH rise caused by the release of ammonia can then be detected by a pH indicator such as bromthymol blue. The lower portion 37 of the syringe 19 is filled with a suitable wash solution, which in particular device described herein is the same as in the syringe 18.

To operate the present device to determine a suspected pregnancy, the syringe 17 is filled with a urine sample and inserted into the receptacle 21. With the syringe 17 in place in the device, the plunger 25 is slowly depressed so that the urine sample flows through the tubes 11 and 12 over a period of about one minute. Next, the plunger 34 of the syringe 18 is fully depressed causing a first wash solution to flow through the tubes 11 and 12 thereby washing out retained urine sample, and then causing a flow of enzyme/antibody conjugate solution to pass through the tubes 11 and 12. An incubation period of at least one minute and conveniently about two minutes should be observed at this point to allow the conjugate time to react with any HCG captured by the anti-HCG held at the tube 11 wall. If required, a longer incubation period may be used to increase the sensitivity of an assay.

After the incubation period has elapsed, the plunger 34 of the syringe 19 is fully depressed causing a second wash solution to flush the conjugate from the tubes 11 and 12, and then causing a flow of substrate/indicator solution to pass through the tubes 11 and 12. If the woman is pregnant and HCG is therefore present, the captured enzyme in the tube 11 will metabolize the substrate and cause the indicator to be activated. Use of a color change indicator such as bromthymol blue in a urea/urease system will give a change in the color of the liquid in the tube 11 from yellow to blue. This color change can be compared with the color in the control tube 12 which should remain yellow. A relatively high concentration of HCG in the test sample will give a color indication almost immediately, however, a low concentration of HCG will require up to 10 minutes to give a positive indicator response.

Because of the aforementioned features of the present device, low levels of HCG on the order of 50 mIU/ml can be detected. This is important so that pregnancy can be diagnosed at an early stage and so that a quick test can be carried out to reliably indicate an ectopic pregnancy.

Figure 3:
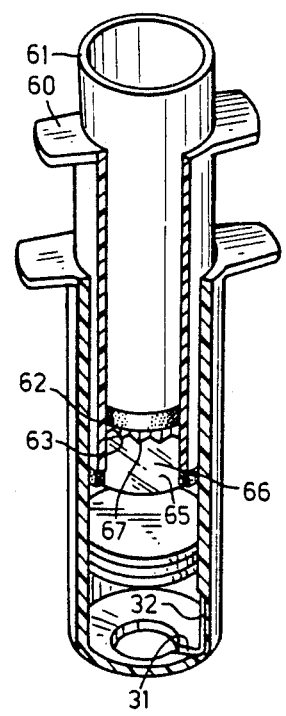
FIG. 3 is a cut away view of an alternate double piston syringe which may be used in the present device.

The preferred enzyme for use in the pregnancy test device of the invention is urease because it is easily detected by the pH rise caused by metabolism of its substrate urea. Also, urea is stable in aqueous solution for at least six months at room temperature. This is in contrast to other substrates such as hydrogen peroxide, used with horseradish peroxidase, which breaks down, rather quickly. However, without refrigeration, urea in water will eventually break down thereby making the device unusable. To provide a device having a long shelf life, i.e. two years, at room temperature, the syringe 19 may be modified as shown in FIG. 3.

The modified syringe 19 has a plunger 60 equipped with a rod 61 slidably disposed longitudinally within it. The rod 61 has a piston 62 affixed at its lower end, and the piston 62 has a piercing member 63 protruding from the lower surface thereof. The plunger 60 has a rupture membrane 65 covering the opening at its lower end, and the chamber 66 created by the membrane 65, the interior of the plunger 60 and the lower end of the rod 61 provides a space for storing powdered urea or other unstable component which may be used in another application. When the pregnancy test is to be performed, the rod 61 is depressed causing the piercing member 63 to rupture the membrane 65 thereby dispensing the powdered urea into the aqueous medium in the upper portion 36 of the syringe 19. The urea will quickly dissolve and the test can be immediately conducted in the manner described above. The piercing member 63 may also assist the dissolution of the powdered urea by causing a portion of it to be retained about the teeth 67 thereof. The retention aids in evenly distributing the powdered urea through the aqueous medium for rapid dissolution.

As mentioned above, syringes 18 and 19 may also be removable, and as such may have a body and outlet as shown in FIG. 1 for the syringe 17. This arrangement would be applicable when different wash solutions are required in the lower portions 37 of the syringes 18 and 19 since in the preferred device just described, such wash solutions are in communication with one another. In this case the separation of the reagents may be simply achieved by means of a suitable rupture membrane placed at the syringe outlet. Conveniently, this membrane is a thin plastic (e.g. polyethylene) impermeable membrane drawn over the syringe outlet. Pressure on the syringe plunger causes distension and rupture of the membrane and release of the syringe contents. In this way, cross contamination by flow or diffusion of a reagent from one syringe to another may be prevented without any requirement for complex or expensive valves.

Finally, in its commercial form, the present device will be sold with a protective hard cover member 70 as shown in FIG. 1. The cover member 70 will fit snugly about a peripheral shoulder 71 about the bottom portion of the body 10 thereby protecting all of the components of the device prior to use. A projection (not shown) within the cover 70 may be desirable to plug the vent 51 while in storage thus preventing evaporation of wash solutions in the lower portions 37 of the syringes 18 and 19. Removal of the cover 70 unplugs the vent 51 in readiness for performance of the test.

I claim:

1. A device for performing an enzyme immunoassay, comprising:
   at least one assay tube having a first and a second end and having an antibody, antigen or hapten attached to an internal surface thereof;
   a first syringe having an outlet connectable to the first end of the assay tube for supplying a flow of a test liquid therethrough;
   a second syringe having an outlet connected to the first end of the assay tube for supplying a flow of a first wash solution followed immediately by a flow of an enzyme conjugate containing solution therethrough, said second syringe having a first piston and a second piston spaced from one another, the first piston being positioned to separate the first wash solution from the conjugate solution, the second piston having a plunger, and said syringe also having a wall with a groove therein connecting the syringe outlet with the conjugate solution only when the first piston is fully depressed; and
   a third syringe having an outlet connected to the first end of the assay tube for supplying a flow of a second wash solution followed immediately by a flow of solution containing an enzyme substrate and an enzyme metabolite indicator therethrough, said third syringe having a first piston and a second piston, spaced from one another, the first piston being positioned to separate the second wash solution from the substrate, the second piston having a plunger, said third syringe also having a wall with a groove therein connecting the syringe outlet with the substrate and indicator solution only when the first piston is fully depressed.

2. A device as claimed in claim 1, wherein the antibody, antigen or hapten is bonded to the internal surface of the assay tube.

3. A device as claimed in claim 1, further comprising a control tube not having any antibody, antigen or hapten attached to an internal surface thereof, the control tube being connected to one end of the assay tube.

4. A device as claimed in claim 1, further comprising means for receiving and storing liquids which have flowed through the assay tube.

5. A device as claimed in claim 4, wherein the means for receiving and storing liquids comprises a reservoir formed integrally with the device.

6. A device as claimed in claim 1, wherein the device is a pregnancy test kit having human chorionic gonadotropin antibody (anti-HCG) attached to the internal surface of the assay tube, the enzyme conjugate being urease/anti-HCG, the enzyme substrate being urea, and the enzyme metabolite indicator being bromthymol blue.

7. A device as claimed in claim 6, wherein the test liquid is urine.

8. A device as claimed in claim 6, wherein the test liquid is blood.

9. A device as claimed in claim 1, wherein the third syringe is provided with a plunger having a rod slidably disposed longitudinally within it, said rod having a piston affixed at its lower end, the piston being equipped with a piercing member protruding from the lower surface thereof and the plunger having a rupture membrane covering an opening at its lower end, said membrane, the interior of the plunger and the lower end of the rod defining a chamber.

10. A device as claimed in claim 9, wherein the device is a pregnancy test kit having human chorionic gonadotropin antibody (anti-HCG) attached to the internal surface of the assay tube, the enzyme conjugate being urease/anti-HCG, the enzyme substrate being urea contained in powder form in said chamber, and the indicator being bromthymol blue.

11. A device as claimed in claim 1, wherein the second and third syringes are each provided with a rupture membrane about each outlet thereof to prevent cross contamination of solutions contained therein.

12. A device as claimed in claim 5, further comprising vent means for the reservoir and a protective hard cover for the device having means integral therewith for plugging the vent means when the cover is in place.

13. A device as claimed in claim 1, wherein the device has a flat bottom surface provided with grooves therein connecting outlets for the first, second and third syringes with the first end of the assay tube, and a base plate for the device which coacts with the grooves to form channels for the flow of liquids from the syringes to the first end of the assay tube.

* * * * *